United States Patent [19]

Griffith et al.

[11] Patent Number: 5,539,120

[45] Date of Patent: Jul. 23, 1996

[54] ARYLALKYL-AMINES HAVING ANTICONVULSANT AND NEUROPROTECTIVE PROPERTIES

[76] Inventors: Ronald C. Griffith, 41 Northfield Gate, Pittsford, N.Y. 14534; James J. Napier, 203 Lake Shore Dr., Lindenhurst, Ill. 60046

[21] Appl. No.: 399,030

[22] Filed: Mar. 6, 1995

Related U.S. Application Data

[62] Division of Ser. No. 915,489, Jul. 16, 1992, Pat. No. 5,430,044, which is a division of Ser. No. 427,661, Oct. 27, 1989, abandoned, which is a continuation-in-part of Ser. No. 232,566, Aug. 12, 1988, abandoned, which is a continuation-in-part of Ser. No. 11,982, Feb. 6, 1987, abandoned.

[51] Int. Cl.$^6$ ....................... C07D 213/02; C07C 211/27
[52] U.S. Cl. ....................... 546/329; 564/366; 564/355; 564/336; 564/373
[58] Field of Search ....................... 564/336, 373, 564/366, 374; 514/649, 654, 655, 332, 357; 546/264, 329; 560/38, 41, 42

[56] References Cited

U.S. PATENT DOCUMENTS

| | | | |
|---|---|---|---|
| 2,503,285 | 4/1950 | McPhee | 564/373 |
| 2,604,473 | 7/1952 | Sperber | 546/329 |
| 3,138,639 | 6/1964 | Brossi et al. | 564/373 |
| 3,420,841 | 1/1969 | Brust et al. | 546/255 |
| 3,471,612 | 1/1969 | Goonewardene | 546/336 |
| 3,510,560 | 5/1970 | Saunders et al. | 564/373 |
| 3,692,784 | 9/1972 | Lindberg | 260/247.2 |
| 3,819,641 | 6/1974 | Welstead, Jr. et al. | 546/329 |
| 3,928,613 | 12/1975 | Berntsson et al. | 514/357 |
| 3,992,389 | 11/1976 | Cavalla et al. | 260/293.76 |
| 4,098,764 | 7/1978 | Gencarelli et al. | 564/336 |
| 4,309,424 | 1/1982 | Martin et al. | 424/244 |
| 4,536,599 | 8/1985 | Masuko et al. | 564/373 |
| 4,769,466 | 9/1988 | Griffith et al. | 564/337 |
| 4,798,687 | 1/1989 | Griffith et al. | 564/194 |
| 4,822,914 | 4/1989 | Martin et al. | 564/373 |
| 4,871,872 | 10/1989 | Griffith | 564/157 |
| 4,873,241 | 10/1989 | Napier et al. | 514/237 |
| 4,968,721 | 11/1990 | Martin et al. | 514/649 |
| 4,996,235 | 2/1991 | Robertson et al. | 514/649 |
| 5,047,541 | 9/1991 | Griffith | 546/225 |
| 5,086,073 | 2/1992 | White et al. | 514/649 |
| 5,093,524 | 3/1992 | Griffith | 564/196 |
| 5,220,068 | 6/1993 | Knoll et al. | 564/374 |
| 5,292,760 | 3/1994 | Martin et al. | 514/357 |
| 5,382,683 | 1/1995 | Griffith | 564/196 |

FOREIGN PATENT DOCUMENTS

| | | |
|---|---|---|
| 570666 | 2/1959 | Canada. |
| 0057870 | 8/1982 | European Pat. Off.. |
| 0173943 | 3/1986 | European Pat. Off.. |
| 0332582 | 7/1989 | European Pat. Off.. |
| 0516978 | 12/1992 | European Pat. Off.. |
| 955508 | 1/1957 | Germany. |
| 7211063 | 4/1972 | Japan. |
| 4818262 | 3/1973 | Japan. |
| 343388 | 2/1960 | Switzerland. |
| WO88/02254 | 4/1988 | WIPO. |

OTHER PUBLICATIONS

CA 64,14162f, abstracting Zaheer et al., *Ann. Chem.* 691, 55–60 (1966).
CA 73,25044n, abstracting Novelli et al., *Bol. Soc. Quim Peru*, 35(3), 77–84 (1969).
CA 77,19586, abstracting Patel et al., *J. Indian Chem. Soc.* 49(2) 177–80 (1972).
CA 85,5705y, abstracting Japan Kokai 50/130776 (1975).
CA 96,19744z, abstracting Antoniadau–Vyza et al, *Prakt. Akad. Athenon* 54 (A–B), 383–97 (1980).
Hubsch et al., "Determination of 2–Amino–N(1–Methyl–1, 2–Diphenylethyl) Acetamide Monohydrochloride From a Ground Beef Matrix High Performance Liquid Chromatography", Abst. 127, *Northeast Regional Meeting of the Am. Chem. Soc.*, Rochester, NY, Nov. 19, 1987.
Palmer et al., "A New Anticonvulsant, PR 934–423 Active Against Maximal Electroshock Seizures I: Mice Studies" Abst. 317.15, *Society of Neuroscience Meetings*, LA (Nov. 16, 1987).
Colombo et al., "A New Anticonvulsant, PR 934–423, Active Against Maximal Electroshock Seizures II: Rat Studies", Abst. 317.16, *Society of Neuroscience Meetings*, LA (Nov. 16, 1987).
Freedman et al., "A New Anticonvulsant, PR 934–423, Active Against Maximal Electroshock Seizures III: Electrophysiological Studies", Abst. 317.17 *Society of Neuroscience Meetings*, New Orleans, LA (Nov. 16, 1987).

(List continued on next page.)

*Primary Examiner*—José G. Dees
*Assistant Examiner*—Deborah Lambkin
*Attorney, Agent, or Firm*—Seidel, Gonda, Lavorgna & Monaco

[57] ABSTRACT

There is provided a method of treatment of neurological disorders, such as epilepsy, stroke and cerebral ischaemia, which comprises the administration of a compound of Formula I:

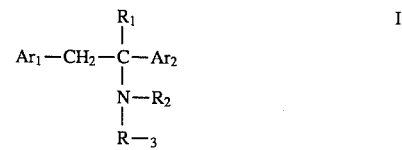

wherein,

Ar$_1$ and Ar$_2$, which may be the same or different, independently represent phenyl or phenyl substituted by one or more of amino, nitro, halogen, hydroxy, C1 to 6 alkoxy, C1 to 6 alkyl or cyano;

R$_1$ represents hydrogen, C1 to 6 alkyl, C1 to 6 alkoxycarbonyl;

R$_2$ represents hydrogen or COCH$_2$NH$_2$;

R$_3$ represents hydrogen or C1 to 6 alkyl;

in addition, when R$_2$ represents hydrogen either one or both of Ar$_1$ and Ar$_2$ may also represent 2-, 3- or 4-pyridinyl and R$_1$ may also represent trihalomethyl;

or a pharmaceutically acceptable salt thereof.

Some of the compounds of formula I are novel, and these are also provided, together with pharmaceutical compositions containing the novel compounds.

27 Claims, No Drawings

OTHER PUBLICATIONS

Luke et al., "Toxicity of a Novel Anticonvulsant, 2-Amino-N-(2-Methyl-1,2-Diphenylethyl) Acetamides PR 934-423A" Abst. *Society of Toxicology Annual Meeting*, Dallas, Tx. (Feb. 15, 1988).

Griffith et al., "Synthesis and Anticonvulsant Activity of a Series of 2-Amino-N-(1,2-Diphenylethyl) Acetamides" Abst. *196th Natl. Meeting of the Am. Chem. Soc.*, Los Angeles, CA (Sep. 25-29, 1988).

Garske et al., "Preclinical Profile of Isomers of the Anticonvulsant PR 934-423", *Society of Neuroscience Meeting*, Toronto, Ont., Can. (Nov. 1988).

Stagnitto et al., "PR 1013-708, A Potent Anticonvulsant Against Maximal Electroshock Seizures (MES) in Rodents", Abs. *Society of Neuroscience Meeting*, Toronto, Ont., Can. (Nov. 1988).

Wilson et al., "Anticonvulsant Concentrations in CSF and Serum of Rats Protected Against MES by PR 934-423A", Abs. *Society of Neuroscience Meeting*, Toronto, Ont., Can. (Nov. 1988).

Palmer et al., "Status of PR 934-423. A Novel Anticonvulsant Targeted for Generalized Toxic/Clinic Seizures New Designation is FPL 12924AA", Abs. *Princeton Symposium*, NJ (May 1989).

Gosh et al., *Arzneim-Forch/Drug Res.* 28 (11) Heft 9 (1978) pp. 1561-1564.

Winn et al., *J. Org. Chem.*, 33(6), 2388-92 (1968).

CA 84(9):59216n, abstracting German Offen. DE 2415063 (1976).

CA 104(17):148472s, abstracting U.S. Patent 4,536,599 (1986).

Medical Subject Headings, Tree Structures, 1992, pp. 165-174.

Dodds, Lawson & Williams, *Royal Society Journal*, 1943.

Shimada et al., *Chem. Pharm. Bull.* 32(12) 4893-906 (1984).

Niemers et al., *Synthesis* (9), 593-5 (1976).

Coughenour et al., *Pharm. Biochem. & Behavior*, vol. 6, pp. 351-353 (1977).

Porter et al., *Cleveland Clinic Quarterly*, 51:293-305, (Summer 1984).

ARYLALKYL-AMINES HAVING ANTICONVULSANT AND NEUROPROTECTIVE PROPERTIES

This is a divisional of application Ser. No. 07/915,489 filed Jul. 16, 1992, U.S. Pat. No. 5,430,044, which is a divisional of application Ser. No. 07/427,661, filed Oct. 27, 1989, now abandoned, which is a continuation-in-part of application Ser. No. 07/232,566, filed Aug. 12, 1988, now abandoned, which is a continuation-in-part of application Ser. No. 07/011,982, field Feb. 6, 1987, now abandoned.

This invention relates to pharmaceutical compounds, some of which are novel, and to their anticonvulsant, sedative and neuroprotective properties.

Compounds which possess anticonvulsant, antihypoxic or N-methyl-(d)-aspartate (NMDA) blocking properties are useful in the treatment and/or prevention of neurodegeneration in pathological conditions such as stroke, cerebral ischaemia, cerebral palsy, hypoglycaemia, epilepsy, Alzheimer's disease, Huntington's chorea, Olivo-ponto-cerebellar atrophy, perinatal asphyxia and anoxia. It has now been discovered that many substituted arylalkyl-amines and -amides possess anticonvulsant and neuroprotective properties which are useful for the treatment of such disorders. Many of these compounds also possess sedative properties.

According to the invention we provide a method of treatment of neurological disorders, such as epilepsy, stroke and cerebral ischaemia, which comprises the administration to a patient in need of such treatment of an effective amount of a compound of Formula I,

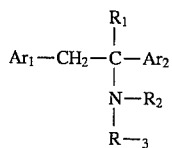

wherein,
$Ar_1$ and $Ar_2$, which may be the same or different, independently represent phenyl or phenyl substituted by one or more of amino, nitro, halogen, hydroxy, C1 to 6 alkoxy, C1 to 6 alkyl or cyano;
$R_1$ represents hydrogen, C1 to 6 alkyl, C1 to 6 alkoxycarbonyl;
$R_2$ represents hydrogen or $COCH_2NH_2$;
$R_3$ represents hydrogen or C1 to 6 alkyl;
in addition, when $R_2$ represents hydrogen either one or both of $Ar_1$ and $Ar_2$ may also represent 2-, 3- or 4-pyridinyl and $R_1$ may also represent trihalomethyl;
or a pharmaceutically acceptable salt thereof.

By halogen we mean fluorine, chlorine, bromine or iodine.

This invention also relates to all stereoisomeric forms, optical enantiomeric forms and pharmaceutically acceptable acid addition salts of the compounds of formula I.

The compounds of formula I possess useful anti-convulsant properties as demonstrated by their ability to inhibit maximal electroshock (MES) induced seizures in mice. The compounds of formula I also possess antihypoxia activity as demonstrated by their ability to increase the survival time of mice in an oxygen depleted environment. In addition, compounds of formula I inhibit the onset of convulsions and death induced by administration of N-methyl-(d)-aspartate (NMDA) to mice.

DETAILED DESCRIPTION

Some of the compounds of formula I are known compounds and are commercially available. Compounds of formula I in which $R_2$ represents hydrogen may be prepared by known procedures for amine formation, for example those given in "Advanced Organic Chemistry", 2nd Ed., J March, (McGraw-Hill) at page 1172. Compounds of formula I in which $R_2$ represents $COCH_2NH_2$ may be prepared by known procedures for amide formation, for example those given in "Advanced Organic Chemistry" at page 1171. Methods for the preparation of compounds of formula I are also given in U.S. Pat. Nos. 4,769,466 and 4,798,687.

A process for the preparation of compounds of formula I in which $R_2$ represents $COCH_2NH_2$ which may be specifically mentioned comprises:

a) removal of the amine protecting group from a compound of formula II in which $P_1$ and $P_2$ together constitute a suitable protecting group, and $Ar_1$, $Ar_2$, $R_1$ and $R_3$ are as defined above:

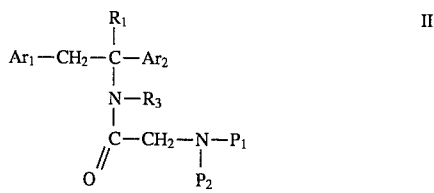

b) aminating a compound of formula III in which $Ar_1$, $Ar_2$, $R_1$ and $R_3$ are as defined above:

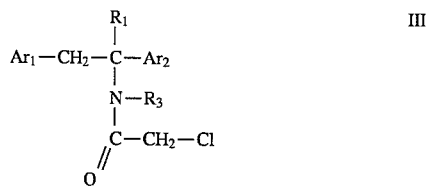

For method a), suitable protecting groups that $P_1$ and $P_2$ may together constitute include: a urethane protecting group such as benzyloxycarbonyl (CBZ) or t-butyloxycarbonyl (BOC); or $P_1$ and $P_2$ together with the nitrogen atom to which they are attached may form a phthalimide group. The amine protecting groups may be removed by either catalytic hydrogenation for the CBZ group, a suitable catalyst being palladium or platinum on carbon, and the reaction being suitably carried out in an inert solvent such as methanol; treatment with an acid such as trifluoroacetic or hydrochloric acid for the BOC group; or treatment with hydrazine in a lower alkanol such as ethanol for the phthalimide group. Compounds of formula II may be prepared by reacting a compound of formula I in which $R_2$ represents hydrogen with a compound of formula IV in which $P_1$ and $P_2$ are as defined above:

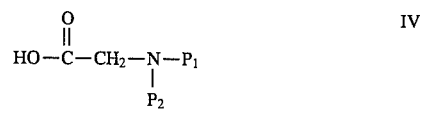

This reaction may be carried out in an inert solvent, such as tetrahydrofuran, in the presence of a coupling reagent such as dicyclohexylcarbodiimide with or without 1-hydroxybenzotriazole or other additives. Compounds of formula IV are commercially available or may be made by known methods.

For method b), the amination reaction may be carried out by reacting a compound of formula III with ammonia in a solvent such as a lower alkanol, for example methanol or ethanol, or a chlorinated solvent, for example chloroform or methylene chloride, or mixtures thereof. Compounds of formula III may be prepared by reacting a compound of formula I in which $R_2$ represents hydrogen with an activated two carbon acid derivative which contains a leaving group e to the carbonyl, such as chloroacetyl chloride, in the presence of an acid acceptor, such as triethylamine.

Certain compounds of formula I are novel, thus according to a further aspect of the invention we provide compounds of formula IA:

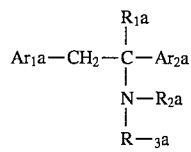

wherein $Ar_1a$, $Ar_2a$, $R_1a$, $R_2a$ and $R_3a$ are defined respectively as $Ar_1$, $Ar_2$, $R_1$, $R_2$ and $R_3$ above provided that when $R_2a$ represents hydrogen, a) $R_1a$ represents C1 to 6 alkyl or C1 to 6 alkoxycarbonyl and b) $Ar_1a$ and $Ar_2a$ do not both represent phenyl, and pharmaceutically acceptable salts thereof.

A group of compounds of formula IA which may be specifically mentioned is that in which $R_1a$, $R_2a$ and $R_3a$ are as defined above, and either one or both of $Ar_1a$ and $Ar_2a$ represents 4-hydroxyphenyl.

We prefer that $Ar_1a$ and $Ar_2a$ represent unsubstituted phenyl. When $Ar_1a$ and $Ar_2a$ are substituted, we prefer that they are mono- or disubstituted.

Where $R_1a$ or $R_3a$ or a substituent on an aromatic ring represents alkyl or alkoxy, we prefer that it contains up to 4 carbon atoms, for example ethyl, propyl and especially methyl. $R_1a$ is preferably hydrogen or, more preferably, methyl. $R_3a$ is preferably hydrogen.

Compounds of formula I which are useful in the methods of treatment or prevention of neurological disorders include:
1,2-diphenylethylamine
1,2-diphenyl-2-propylamine
1,2-bis(4-fluorophenyl)-2-propylamine
1,2-diphenyl-2-butylamine
(−)1,2-diphenyl-2-propylamine
(+)1,2-diphenyl-2-propylamine
2,3-diphenyl-2-aminopropanoic acid methyl ester
N-methyl-1,2-diphenyl-2-propylamine
N-methyl-1,2-diphenylethylamine
1-(3-nitrophenyl)-2-phenyl-2-propylamine
1-(3-chlorophenyl)-2-phenyl-2-propylamine
1-(3-bromophenyl)-2-phenyl-2-propylamine
1-(3-cyanophenyl)-2-phenyl-2-propylamine
2-(2-methylphenyl)-1-phenyl-2-propylamine
1-(4-chlorophenyl)-2-phenyl-2-propylamine
1-phenyl-2-(3,4-dichlorophenyl)-2-propylamine
1-phenyl-2-(3-methoxyphenyl)-2-propylamine
1-(4-hydroxyphenyl)-2-phenyl-2-propylamine
1-(4-hydroxyphenyl)-2-phenylethylamine
1-phenyl-2-(4-hydroxyphenyl)ethylamine
1,2-bis(4-hydroxyphenyl)ethylamine
1-phenyl-2-(4-hydroxyphenyl)-2-propylamine 1,2-bis(4-hydroxyphenyl)-2-propylamine
1-(2-pyridinyl)-2-phenylethylamine
1-(3-pyridinyl)-2-phenylethylamine
1-(4-pyridinyl)-2-phenylethylamine
1-phenyl-2-(2-pyridinyl)ethylamine
1-phenyl-2-(3-pyridinyl)ethylamine
1-phenyl-2-(4-pyridinyl)ethylamine
N-methyl-1-(3-pyridinyl)-2-phenylethylamine
3,3,3-trifluoro-1,2-diphenyl-2-propylamine
N-methyl-3,3,3-trifluoro-1,2-diphenyl-2-propylamine
2-amino-N-(1,2-diphenyl-1-methylethyl)acetamide
2-amino-N-(1,2-diphenylethyl)acetamide
2-amino-N-[1,2-bis(4-fluorophenyl)-1-methylethyl]acetamide The compounds of general formula I are basic compounds and may be used as such or pharmaceutically acceptable acid addition salts may be prepared by treatment with various inorganic or organic acids, such as hydrochloric, hydrobromic, sulfuric, phosphoric, acetic, lactic, succinic, fumaric, malic, maleic, tartaric, citric, benzoic, methanesulfonic or carbonic acids.

For the above mentioned uses the dosage administered will, of course, vary with the compound employed, the mode of administration and the treatment desired. However, in general, satisfactory results are obtained when the compounds are administered at a daily dosage of from about 0.1 mg to about 20 mg per kg of animal body weight, preferably given in divided doses 1 to 4 times a day or in sustained release form. For man the total daily dose is in the range of from 5 mg to 1,400 mg more preferably from 10 mg to 100 mg, and unit dosage forms suitable for oral administration comprise from 2 mg to 1,400 mg of the compound admixed with a solid or liquid pharmaceutical carrier or diluent.

The compounds of formula I, and pharmaceutically acceptable derivatives thereof, may be used on their own or in the form of appropriate medicinal preparations for enteral or parenteral administration.

According to the invention there is also provided a pharmaceutical composition comprising preferably less than 80% and more preferably less than 50% by weight of a compound of formula I, or a pharmaceutically acceptable salt thereof, in admixture with a pharmaceutically acceptable adjuvant, diluent or carrier.

Examples of such adjuvants, diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, i.e. oesophageal administration include tablets, capsules and dragees;

sustained release compositions include those in which the active ingredient is bound to an ion exchange resin which is optionally coated with a diffusion barrier to modify the release properties of the resin.

We prefer the composition to contain up to 50% and more preferably up to 25% by weight of the compound of formula I, or of the pharmaceutically acceptable derivative thereof.

The compounds of formula I and pharmaceutically acceptable derivatives thereof have the advantage that they are less toxic, more efficacious, are longer acting, have a broader range of activity, are more potent, produce fewer side effects, are more easily absorbed or have other useful pharmacological properties, than compounds of similar structure.

The compounds of general formula I possess useful pharmaceutical properties. In particular they possess useful antiepileptic properties, antihypoxia activities and/or NMDA blocking activities. These activities were assessed by standard methods.

Antiepileptic activity was measured by assessing a compound's ability to prevent the hind limb tonic extension component of the seizure in groups of mice induced by maximal electroshock (MES) after oral or intraperitoneal administration according to the procedures of the Epilepsy Branch, NINCDS as published by R. J. Porter, et at., Cleve. Clin. Quarterly 1984, 51, 293, and compared to the standard agents dilantin and phenobarbital. Activities ($ED_{50}$'s) in the range of 10–400 m/k after oral administration in this assay system were obtained.

The compounds of this invention possess useful antihypoxia activity, that is, they extend the lifetime of animals exposed to a hypoxic environment. This activity is conveniently measured in mice. Groups of mice are tested at various times after the intraperitoneal administration of graded doses of the test compound. The animals' survival time in a temperature controlled hypoxic environment (96% nitrogen and 4% oxygen) is recorded. A statistical comparison is made between coincident vehicle treated animals and the experimental group. The dose-response and minimum active dose (MAD) for compounds are obtained. Other modes of administration can also be used.

NMDA blocking activity was measured by assessing a compound's ability to protect mice from convulsions induced by intravenous administration of 150 m/k of NMDA according to the procedures of Czuczwar et al., (Neurotransmitters, Seizures and Epilepsy III, edited by G. Nistico et al., Raven Press, New York 1986, pages 235–246). Groups of mice were pretreated by 30 min with the test compound by the oral or intraperitoneal routes and then given NMDA. Animals were observed for convulsions as defined by loss of righting reflex. Animals were kept for 60 min after NMDA dosing and mortality was recorded.

NMDA and glycine receptor affinity was also tested in the [$^3$H]L-glutamate and [$^3$H]glycine binding assays following the method of Monaghan & Cotman, PNAS, 83, 7532, (1986) and Watson et al, Neurosci. Res. Comm., 2, 169, (1988).

The following in vitro methods are also used to measure NMDA blocking activity: NMDA (20 μM) is applied to tissue slices of rat hippocampus (450 μm thick) for approximately 2 minutes causing a massive depolarisation of hippocampal neurons, and a profound reduction of the synaptic field potential. The test is repeated seveal times to obtain a base line response. The compound under investigation is then included in the buffer bathing the slice, and NMDA is reapplied. The ability of the compound to block the reduction in field potential produced by NMDA is then determined.

In a second in vitro assay, rat hippocampal slices (450 m thick) are pretreated with a buffer containing 10 μM 6,7-dinitroquinoxaline-2,3-dione (DNQX) and magnesium (25 μM). Under these conditions the synaptic response is almost entirely mediated by NMDA receptors. To evaluate NMDA antagonism, the test compounds are added to the buffer and the synaptic field potentials are compared before and during treatment. The decrease in response caused by the drug is expressed as a percentage of the pre-drug response.

The following compounds of formula I or their acid salts were either commercially available or prepared as described in the aforementioned literature:

1,2-diphenyl-2-propylamine
1,2-bis(4-fluorophenyl)-2-propylamine
1,2-diphenyl-2-butylamine
(−)1,2-diphenyl-2-propylamine
(+)1,2-diphenyl-2-propylamine
2,3-diphenyl-2-aminopropanoic acid methyl ester
N-methyl-1,2-diphenyl-2-propylamine
N-methyl-1,2-diphenylethylamine
1-(2-pyridinyl)-2-phenylethylamine
1-(3-pyridinyl)-2-phenylethylamine
1-(4-pyridinyl)-2-phenylethylamine
1-phenyl-2-(2-pyridinyl)ethylamine
1-phenyl-2-(3-pyridinyl)ethylamine
1-phenyl-2-(4-pyridinyl)ethylamine
N-methyl-1-(3-pyridinyl)-2-phenylethylamine
3,3,3-trifluoro-1,2-diphenyl-2-propylamine
N-methyl-3,3,3-trifluoro-1,2-diphenyl-2-propylamine Additional examples of the compounds of formula I were prepared as described below.

EXAMPLE 1

Preparation of
1-(4-Hydroxyphenyl)-2-phenyl-2-propylamine hydrochloride a) Preparation of 1-[4-(Phenylmethoxy)phenyl]-2-phenyl-2-propylamine maleate To a stirred suspension of α-methyl-α-[[4-(phenylmethoxy)phenyl]-methyl]benzeneacetic acid (12.9 g, 0.372 mol, prepared by the reaction of the dilithium salt of 2-phenylpropionic acid with 4-(phenylmethoxy)benzyl bromide in benzene (200 mL) under nitrogen were added triethylamine (5.2 mL, 0.037 mol) and diphenylphosphoryl azide (8.4 mL, 0.037 mol) and the solution was heated to reflux for 2 hours. To the reaction was added 2,2,2-trichloroethanol (17.4 mL, 0.18 mol) and the reaction was heated at reflux for 20 h. The reaction mixture was cooled to ambient, diluted with ethyl acetate (100 mL), washed with water (75 mL), 1N HCl (75 mL), 1N NaOH (75 mL), saturated NaCl (100 mL), dried over magnesium sulfate, and the solvent removed to provide 40.2 g of an oil. This oil was dissolved in tetrahydrofuran (100 mL) and 90% acetic acid (200 mL), and the solution cooled to 5° C. Zinc dust (60 g, 0.92 mol) was added, the mixture was warmed to ambient temperature and stirred overnight. The reaction mixture was filtered and the filtrate was concentrated to an oil. This oil was dissolved in ethyl acetate (200 mL) and water (100 mL), basified with solid sodium carbonate, filtered, the phases separated, and the aqueous phase extracted with ethyl acetate (200 mL). The combined ethyl acetate extracts were washed with saturated NaCl, dried over magnesium sulfate, and the solvent removed to provide 13.1 g of an oil. This oil was purified by silica gel chromatography on a Waters Prep 500, eluting with ammoniated 3%-methanol/methylene chloride to provide 10.6 g of an oil. To a solution of this oil (4.0 g) in ethyl acetate (50 mL) was added maleic acid (1.5 g, 0.013 mol). The solid which formed was isolated by filtration and vacuum dried to provide 2.9 g of 1-[4-(phenylmethoxy)phenyl]-2-phenyl-2-propylamine maleate, mp 180°–181° C.

b) Preparation of 1-(4-Hydroxyphenyl)-2-phenyl-2-propylamine hydrochloride

To a solution of 1-[4-(phenylmethoxy)phenyl]-2-phenyl-2-propylamine (4.2 g, 0.013 mol) in methanol (200 mL), 1N hydrochloric acid (50 mL) and tetrahydrofuran (50 mL) was added 5% palladium on carbon (0.9 g). The mixture was shaken on a Parr apparatus under a pressure of 35–40 psi of hydrogen for 16 h. The catalyst was removed by filtration and the majority of the solvent removed under vacuum. The residue was basified with 1N sodium bicarbonate (100 mL) and extracted with chloroform (4×100 mL). The combined chloroform extracts were washed with saturated sodium chloride (75 mL) and dried over magnesium sulfate. Removal of solvent gave 3.0 g of an oil. This oil was dissolved in methanol (60 mL), acidified with gaseous HCl and diluted with ether (120 mL). The solid which formed was isolated by filtration and vacuum dried at 70° C. for 60 hours to provide 1.6 g of 1-(4-hydroxyphenyl)-2-phenyl-2-propylamine hydrochloride; mp 247°–248° C.

EXAMPLE 2

Preparation of
1-(4-Hydroxyphenyl)-2-phenylethylamine hydrochloride a) Preparation of 2-Phenyl-1-[4-(phenylmethoxy)phenyl]ethylamine hydrochloride To a solution of lithium bis(trimethylsilyl)amide (0.047 mol) in tetrahydrofuran (80 mL) and hexane (30 mL) at 0° C. under nitrogen was added a solution of 4-(phenylmethoxy)benzaldehyde (10.0 g, 0.047 mol). The solution was stirred at approximately 4°–10° C. for 45 min and a solution of benzylmagnesium chloride (23 mL of 2M THF solution, 0.046 mol) was added. The solution was allowed to warm to ambient temperature and stirred at that temperature overnight. The solution was cooled in an ice-water bath and saturated ammonium chloride (5.7 mL) was added. The precipitate solid was removed by filtration and the filtrate concentrated to give 13.9 g of an oil. This was dissolved in 2-propanol (50 mL) and acidified with gaseous HCl. The white solid which formed was isolated by filtration and dried to give 11.78 g of 2-phenyl-1-[4-(Phenylmethoxy)phenyl] ethylamine hydrochloride; mp 203°–204° C.

b) Preparation of 1,-(4-Hydroxyphenyl)-2-phenylethylamine hydrochloride

To a solution of 1-[4-(phenylmethoxy)phenyl]-2-phenylethylamine (4.5 g, 0.013 mol) in methanol (200 mL) and 1N hydrochloric acid (50 mL) was added 5% palladium on carbon (0.8 g). The mixture was shaken on a Parr apparatus under a pressure of 35–40 psi of hydrogen for 3 h. The catalyst was removed by filtration, and the filtrate concentrated under vacuum to give a white solid. This solid was recrystallized from 2-propanol (75 mL) and ether (50 mL) and vacuum dried at 80° C. for 48 h to give 2.31 g of 1-(4-hydroxyphenyl)-2-phenylethylamine hydrochloride; mp 203°–204° C.

EXAMPLE 3

Preparation of
1-Phenyl-2-(4-hydroxyphenyl)ethylamine maleate a) Preparation of 1-Phenyl-2-[4-(phenylmethoxy)phenyl]ethylamine hydrochloride By procedures essentially the same as those described in Example 1a and by substituting α-[[(4-phenylmethoxy)phenyl]methyl]benzeneacetic acid (prepared from the reaction of the dilithium salt of benzeneacetic acid with 4-(phenylmethoxy)benzyl bromide) for α-methyl-α-[[4-(phenylmethoxy)phenyl]methyl]benzeneacetic acid; the corresponding 1-phenyl-2-[4-(phenylmethoxy)phenyl]ethylamine hydrochloride 209°–210° C., was prepared.

b) Preparation of 1-Phenyl-2-(4-hydroxyphenyl)ethylamine maleate

To a solution of 1-phenyl-2-[4-(phenylmethoxy)phenyl]ethylamine (4.2 g, 0.012 mol) in methanol (150 mL) and 1N hydrochloric acid (40 mL) was added 5% palladium on carbon (0.5 g). The mixture was shaken on a Parr apparatus under a pressure of 40 psi of hydrogen for 18 h. The catalyst was removed by filtration, and the filtrate was concentrated under vacuum to give a white solid. Two recrystallizations from 2-propanol, methanol and ether gave 3.68 g of a white solid. The above solid (3.3 g) was partitioned between 1N NaHCO$_3$ and a mixture of chloroform, methylene chloride and methanol (50-50-15 mL). The aqueous solution was extracted with methylene chloride (2×100 mL). The combined organic extracts were washed with saturated sodium chloride (75 mL) and dried over magnesium sulfate. Removal of solvent gave 2.3 g of a white solid. The above solid was treated with maleic acid (1.3 g) in ethyl acetate/methanol to provide 2.07 g of 1-phenyl-2-(4-hydroxyphenyl)ethylamine maleate; mp 181°–182° C.

EXAMPLE 4

Preparation of 1,2-Bis(4-hydroxyphenyl)ethylamine fumarate a) Preparation of 1,2-Bis[(4-phenylmethoxy)phenyl]-2-propylamine hydrochloride By procedures essentially the same as those described in Example 1a, the title compound, mp 185°–187° C., was prepared.

b) Preparation of 1,2-Bis(4-hydroxyphenyl)ethylamine fumarate

To a solution of 1,2-bis[4-(Phenylmethoxy)phenylethyl amine (9.60 g, 0.0216 mol) in methanol (300 mL) and 1N hydrochloric acid (30 mL) was added 5% palladium on carbon (1.1 g). The mixture was shaken on a Parr apparatus under a pressure of 40 psi of hydrogen for 17 h. The catalyst was removed by filtration through celite, and the filtrate was concentrated under vacuum to give 5.6 g of a white solid. The above solid was recrystallized from methanol, isopropanol and ether to give 4.62 g of a white solid.

To a suspension of the above solid (3.6 g) in water (50 mL) were added 1N sodium bicarbonate (50 mL), ethyl acetate (100 mL) and methanol (5 mL). The phases were separated and the aqueous phase was extracted with ethyl acetate (2×100 mL). The combined organic extracts were washed with saturated sodium chloride (50 mL) and dried over magnesium sulfate. Removal of solvent gave 2.6 g of a white solid. The above solid was dissolved in ethyl acetate (80 mL) and methanol and treated with maleic acid. The solution was diluted with ethyl acetate (30 mL), concentrated to a volume a 40 mL, and again diluted to a volume of 80 mL with ethyl acetate to provide a white solid. This solid was vacuum dried at 60° C. for 72 h to provide 2.6 g of 1,2-bis(4-hydroxyphenyl)ethylamine fumarate, mp 275°–277° C. (D).

EXAMPLE 5

Preparation of
1-Phenyl-2-(4-hydroxyphenyl)-2-propylamine
hydrochloride a) Preparation of 1-Phenyl-2-[4-(phenylmethoxy)phenyl-2-propylamine maleate By procedures essentially the same as those described in Example 1a, the title compound, mp 154°–155° C., was prepared.

b) Preparation of 1-Phenyl-2-(4-hydroxyphenyl)- 2-propylamine hydrochloride

To a solution of 1-phenyl-2-[4-(phenylmethoxy)phenyl)-2-propylamine (3.50 g, 0.011 mol) in methanol (100 mL), tetrahydrofuran (50 mL) and 1N hydrochloric acid (20 mL) was added 5% palladium on carbon (0.8 g) and the mixture was shaken on a Parr apparatus at approximately 40 psi for 6 h. The catalyst was removed by filtration and the solvent removed under vacuum. Crystallization from 2-propanol and ether and vacuum drying at 80° C. for 48 h provided 1.3 g of 1-phenyl-2-(4-hydroxyphenyl)-2-propylamine hydrochloride; mp 160°–161° C.

EXAMPLE 6

Preparation of
1,2-Bis(4-hydroxyphenyl)-2-propylamine acetate a) Preparation of 1,2-Bis[4-(phenylmethoxy)phenyl]-2-propylamine fumarate By a procedure essentially the same as that described in Example 1a, the title compound, mp 161°–163° C., was prepared.

b) Preparation of 1,2-Bis(4-hydroxyphenyl)-2-propylamine acetate

To a solution of 1,2-bis[4-(phenylmethoxy)phenyl]-2-propylamine (4.56 g, 0.011 mol) in tetrahydrofuran (200 mL), and acetic acid (50 mL) was added 5% palladium on carbon (0.8 g). The mixture was shaken on a Parr apparatus in an atmosphere of 35–40 psi of hydrogen for 16 h. The catalyst was removed by filtration, and the filtrate concentrated under vacuum to provide an oil (6.6 g). Crystallization of this oil from ethyl acetate and methanol and vacuum drying at 60° C. for 48 h provided 1.80 g of 1,2-bis(4-hydroxyphenyl)-2-propylamine acetate; mp 157°–159° C.

EXAMPLE 7

Preparation of
1-(3-Nitrophenyl)-2-phenyl-2-propylamine fumarate

To a suspension of sodium cyanide (34.3 g, 0.7 mol) in glacial acetic acid (500 ml) and n-butylether (100 ml) at 0° C. was added portionwise concentrated sulphuric acid (200 ml). The ice bath was removed and a solution of 1-(3-nitro-phenyl)-2-phenyl-1-propene (prepared from [(3-nitrophenyl)methylene]triphenylphosphorane and acetophenone, 0.5mol) in n-butylether (100 ml) was added dropwise over a period of 2 hours, then the mixture stirred for 48 hours. The mixture was poured into 1000 ml ice, and extracted with chloroform. The extracts were washed with water, dried and evaporated to a solid residue which was stirred with hexane (500 ml), filtered and dried to give N-formyl-1-(3-nitrophenyl)-2-phenyl-2-propylamine. This was treated with fumaric acid in ethyl acetate/isopropanol to give the title compound in 97% yield. Mp 234°–235° C.

EXAMPLE 8

Preparation of
1-(3-chlorophenyl)-2-phenyl-2-propylamine maleate

To a solution of N-formyl-1-(3-nitrophenyl)-2-phenyl-2-propylamine (5.0 g, 0.017 mol) in methanol (200 ml) was added 10% Pd/C catalyst (0.5 g) and the mixture hydrogenated at 50 psi in a Parr apparatus for 3 hours. The catalyst was removed by filtration and the solvent evaporated to a white solid, 4.6 g. This solid was recrystallised from isopropanol (50 ml) to give 2.6 g of N-formyl-1-(3-aminophenyl)-2-phenyl-2-propylamine, mp 114°–115° C. To a stirred solution of sodium nitrate (2.0 g, 0.03 mol) in sulphuric acid (15 ml) at 0° C. under nitrogen was added dropwise a solution of N-formyl-1-(3-aminophenyl)-2-phenyl-2-propylamine (7.0 g, 0.027 mol) in acetic acid (75 ml) and the solution was stirred 2.5 hours at a temperature less than 20° C. The above mixture was added to a solution of cuprous chloride (5.3 g, 0.054 mol) in concentrated HCl (50 ml) at 15° C., and the resulting solution was stirred at that temperature for 1 hour. The reaction mixture was poured into water (500 ml), basified with concentrated ammonium hydroxide, and extracted with chloroform (3×200 ml). The combined chloroform extracts were dried over magnesium sulphate and the solvent evaporated to a solid, 7.5 g. This solid was recrystallised from isopropanol (20 ml) to provide 3.2 g of N-formyl-1-(3-chlorophenyl)-2-phenyl-2-propylamine, mp 108°–109° C.

To a stirred solution of N-formyl-1-(3-chlorophenyl)-2-phenyl-2-propylamine (5.5 g, 0.017 mol) in methanol (100 ml) was added 1N HCl (100 ml) and the mixture was heated to 55°–60° C. for 24 hours. The solvents were removed, the residue suspended in 10% NaOH (500 ml), and extracted with chloroform (3×300 ml). The combined chloroform extracts were dried over magnesium sulphate and the solvent removed to provide 4.3 g of an oil. This oil was treated with maleic acid in ethyl acetate to provide the title compound, mp 151°–152° C.

EXAMPLE 9

Preparation of
1-(3-Bromophenyl)-2-phenyl-2-propylamine maleate

By procedures essentially the same as those described in Example 8, and by substituting cuprous bromide for cuprous chloride and 48% HBr for conc. HCl, the title compound was prepared. Mp 148°–149° C.

EXAMPLE 10

Preparation of
1-(3-Cyanophenyl)-2-phenyl-2-propylamine maleate

By procedures essentially the same as those described in Example 8, and by substituting cuprous cyanide for cuprous chloride and water for conc. HCl, the title compound was prepared. Mp 157°–158° C.

EXAMPLE 11

Preparation of
2-(2-Methylphenyl)-1-phenyl-2-propylamine fumarate

To a stirred solution of o-tolylacetic acid (50.0 g, 0.33 mol) in tetrahydrofuran (400 ml) and hexamethylphosphoric triamide (116 ml, 0.668 mol) at 0° C. was added n-butyllithium (416 ml of 1.6M hexane solution, 0.666 mol). The solution was warmed to ambient temperature and stirred for 0.5 hour. The solution was cooled to −78° C. and iodomethane (20.7 ml, 0.33 mol) was added and the reaction allowed to warm to room temperature and stirred for 45 minutes. The reaction mixture was cooled to 0° C. and n-butyllithium (208 ml of 1.6M hexane solution, 0.333 mol) was added. The reaction was warmed to ambient temperature for 10 minutes, recooled to 0° C. and benzyl bromide (40.4 ml, 0.333 mol) was added. The reaction mixture was warmed to ambient temperature and stirred at that temperature overnight. The reaction was poured into 1N HCl and extracted with ethyl acetate. The organic solution was washed with water (2×) saturated sodium chloride, and dried over magnesium sulphate. Removal of the solvent gave 111 g of an oil. To a solution of the above oil (111 g) in toluene (600 ml) were added triethylamine (51 ml, 0.36 mol) and diphenylphosphoryl azide (82.5 ml, 0.38 mol) and the solution was heated to reflux under nitrogen for 2 hours. Benzyl alcohol (138 ml, 1.3 mol) was added and the solution was refluxed overnight. The reaction was cooled to ambient temperature, diluted with ethyl acetate (300 ml), washed with 1N HCl (2×), 5% sodium hydroxide (2×), saturated sodium chloride, dried over magnesium sulphate, and the solvent removed to provide 300 g of an oil. The above oil (300 g) was dissolved in methanol (1.81) and 3N HCl (200 ml) and hydrogenated at 40 psi of hydrogen over 10% Pd/C (17.4 g) for 2 hours. The catalyst was removed by filtration and the solvents evaporated. The residue was dissolved in chloroform (300 ml) and washed with 1N sodium carbonate (2×300 ml), saturated sodium chloride and dried over magnesium sulphate. Removal of solvent gave an oil which was purified by silica gel chromatography, elution with ammoniated 25% ethyl acetate-hexane, to provide 14.5 g of 2-(2-methylphenyl)-1-phenyl-2-propylamine as an oil. The above oil (0.5 g) was treated with fumaric acid in ethyl acetate/isopropanol to provide 0.35 g of the title compound, mp 180°–182° C.

EXAMPLE 12

Preparation of
1-(4-Chlorophenyl)-2-phenyl-2-propylamine
maleate

By procedures essentially the same as those described in Example 8, the title compound was prepared, mp 174.5°–175.5° C.

EXAMPLE 13

Preparation of
1-Phenyl-2-(3,4-Dichlorophenyl)-2-propylamine
maleate

By procedures essentially the same as those described in Example 8, the title compound was prepared, mp 164°–165° C.

EXAMPLE 14

Preparation of
1-Phenyl-2-(3-methoxyphenyl)-2-propylamine
maleate

By procedures essentially the same as those described in Example 11, the title compound was prepared, mp 139°–140° C.

EXAMPLE 15

Preparation of 1-Phenyl-2-[3-((2,2,2-trichloroethoxycarbonyl)amino)phenyl]-2-propylamine tosylate By procedures essentially the same as those described in Example 7, the title compound was prepared. Mp 237°–239° C.

EXAMPLE 16

Preparation of
2-(3-Chlorophenyl)-1-phenyl-2-propylamine
maleate

By procedures essentially the same as those described in Example 8, the title compound was prepared. Mp 174°–175° C.

EXAMPLE 17

Preparation of
1-(2-Chlorophenyl)-2-phenyl-2-propylamine
maleate

By procedures essentially the same as those described in Example 8, the title compound was prepared. Mp 169°–171° C.

EXAMPLE 18

Preparation of
2-(2-Chlorophenyl)-1-phenyl-2-propylamine
fumarate

By procedures essentially the same as those described in Example 8, the title compound was prepared. Mp 191°–193° C.

EXAMPLE 19

Preparation of
2-(3-Nitrophenyl)-1-phenyl-2-propylamine maleate

By procedures essentially the same as those described in Example 8, the title compound was prepared. Mp 152°–153° C.

EXAMPLE 20

Preparation of
2-(4-Chlorophenyl)-1-phenyl-2-propylamine
maleate

By procedures essentially the same as those described in Example 8, the title compound was prepared. Mp 171.5°–173° C.

EXAMPLE 21

Preparation of
2-(3,4-Dimethoxyphenyl)-1-phenyl-2-propylamine
fumarate

By procedures essentially the same as those described in Example 8, the title compound was prepared. Mp 185° C. (D).

EXAMPLE 22

Preparation of
2-(4-methylphenyl)-1-phenyl-2-propylamine
maleate

By procedures essentially the same as those described in Example 8, the title compound was prepared. Mp 169° C. (D).

EXAMPLE 23

Preparation of
2-(4-methoxyphenyl)-1-phenyl-2-propylamine
maleate

By procedures essentially the same as those described in Example 8, the title compound was prepared. Mp 169°–170° C.

EXAMPLE 24

Preparation of
1-(3,4-Dichlorophenyl)-1-phenyl-2-propylamine
maleate

By procedures essentially the same as those described in Example 8, the title compound was prepared. Mp 175°–176° C.

EXAMPLE 25

Preparation of
1-(4-methoxyphenyl)-2-phenyl-2-propylamine
maleate

By procedures essentially the same as those described in Example 8, the title compound was prepared. Mp 167°–168° C.

EXAMPLE 26

Preparation of
2-Amino-N-(1,2-diphenyl-1-methylethyl)acetamide
hydrochloride

To a stirred solution of 1,2-diphenyl-2-propylamine (21.0 g, 0,085 mol) in chloroform (500 ml) under nitrogen was added N-CBZ-glycine (23.0 g, 0.11 mol), and then a solution of dicyclohexylcarbodiimide (20.6 g, 0.1 mol) in chloroform (100 ml) and the mixture stirred for 14 hours. The precipitated solid was removed by filtration and the solvent evaporated. The residue was dissolved in methylene chloride (500 ml), filtered and evaporated to a yellow oil. This was treated with ether (700 ml) and 500 ml of ice cold water, basified with 5 ml of 50% NaOH, the layers shaken and separated. The ether layer was washed with water (2×125 ml), dried and evaporated to an oil, 33.5 g. This was dissolved in methanol (500 ml) and 10% HCl (50 ml) and hydrogenated at 40 psi in a Parr apparatus over 3.0 g of 10% Pd/C catalyst for 4 hours. The catalyst was removed by filtration, and the solvent evaporated to a white solid. This was dissolved in 80 ml of hot methanol and treated with 200 ml of ether. Upon cooling a solid crystallised which was recrystallised from 100 ml of isopropanol and 100 ml of methanol to give 8.4 g of 2-amino-N-(1,2-diphenyl-1-methylethyl)acetamide hydrochloride which, after vacuum drying at 80° C. for 24 hours, had mp 253°–254° C.

EXAMPLE 27

Preparation of
2-Amino-N-[1,2-bis(4-fluorophenyl)-1-methylethyl]acetamide

To a stirred solution of 1,2-bis(4-fluorophenyl)-2-propylamine (12.0 g, 0.049 mol) in chloroform (200 ml) under nitrogen was added N-CBZ-glycine (10.16 g, 0.049 mol) and then a solution of dicyclohexylcarbodiimide (11.35 g, 0.055 mol) in chloroform (100 ml) and the mixture stirred for 30 minutes, then filtered and the solvent evaporated. The residue was treated with ethyl acetate (200 ml), filtered, an additional 200 ml of ethyl acetate added, and then washed with cold 1% HCl (200 ml), brine (200 ml), dried, and the solvent evaporated to give a pale yellow oil. This was dissolved in methanol (400 ml) and 10% HCl (35 ml) and hydrogenated at 40 psi in a Parr apparatus over 2.5 g of 5% Pd/C catalyst for 2.5 hours. The catalyst was removed by filtration, solvent evaporated and the residue dissolved in water (300 ml) and chloroform (500 ml), basified to pH 11 with 50% NaOH, shaken and separated. The aqueous phase was extracted with chloroform (2×200 ml) and the combined organic phases washed with water (2×150 ml), brine (150 ml), dried and evaporated to a pale yellow oil which solidified on standing. The solid was recrystallised three times from cyclohexane (150 ml) and ethanol (10 ml) and vacuum dried to give 4.44 g of 2-amino-N-[1,2bis(4-fluorophenyl)-1-methylethyl]acetamide, mp 130°–131° C.

EXAMPLE 28

Preparation of
2-Amino-N-(1-ethyl-1,2-diphenylethyl)acetamide

By procedures essentially the same as those described in Example 26, the title compound was prepared. Mp 108.5°–109.5° C.

EXAMPLE 29

Preparation of
2-amino-N-(1,2-diphenylethyl)acetamide
hydrochloride

By procedures essentially the same as those described in Example 26, the title compound was prepared. Mp 197°–199° C.

EXAMPLE 30

Preparation of 2-Amino-N-[1,2-diphenyl-1-(methoxycarbonyl)ethyl]acetamide maleate To a stirred solution of 2,3-diphenyl-2-aminopropanoic acid methyl ester (7.0 g, 0.0275 mol) in chloroform (210 ml) under nitrogen was added N-CBZ-glycine (6.31 g, 0.028 mol) and then dropwise a solution of dicyclohexylcarbodiimide (6.22 g, 0.028 mol) in chloroform (84 ml), and the mixture stirred for 20 hours. Precipitated solids were removed by filtration, and the solvent evaporated to an oily residue which was dissolved in ethyl acetate (200 ml), filtered, washed with 1N HCl (200 ml), 1N sodium carbonate (200 ml) and brine (200 ml), then dried and evaporated to an oily residue, 14.29 g. 12.5 g of this material was dissolved in methanol (210 ml) and 1N HCl (60 ml) and hydrogenated at 40 psi in a Parr apparatus over 1.0 g of 10% Pd/C catalyst for 3 hours. The catalyst was removed by filtration and the solvent evaporated to a semi-solid residue. This was dissolved in water (100 ml) and ethyl acetate (100 ml) and basified with 1N sodium carbonate. The layers were separated, the aqueous layer extracted with ethyl acetate (2×100 ml) and the combined organic layers washed with brine and dried. This solution was treated with 3.25 g of maleic acid and evaporated to an off-white solid, 9.89 g. This was recrystallised from 100 ml of 1:1 methanol:ethyl acetate to give after drying 4.58 g of the title compound as a white solid, mp 163°–165° C.

EXAMPLE 31

Preparation of (+)-2-Amino-N-(1,2-diphenyl-1-methylethyl)acetamide fumarate

The title compound was prepared by the method of Example 26, but using (−)-1,2-diphenyl-2-propylamine as the starting material. Mp 169°–170° C., $[\alpha]_D$=9.4° (C=2, CH$_3$OH).

EXAMPLE 32

Preparation of
(−)-2-Amino-N-(1,2-diphenyl-1-methylethyl)acetamide
fumarate

The title compound was prepared by the method of Example 26, but using (+)-1,2-diphenyl-2-propylamine as the starting material. Mp 171°–172° C., $[\alpha]_D$=9.4° (C=2, CH$_3$OH).

EXAMPLE 33

Preparation of
2-Amino-N-methyl-N-(1,2-diphenylethyl)acetamide maleate

To a stirred solution of N-methyl-1,2-diphenylethylamine (25.95 g, 0.123 mol) and triethylamine (44.5 ml), 0.32 mol) in methylene chloride (300 ml) at 4° C. under nitrogen, was added dropwise a solution of chloracetyl chloride (12.9 ml, 0.16 mol) in methylene chloride (50 ml). The ice bath was removed and the mixture stirred overnight. Water (300 ml) was added and the layers separated. The aqueous layer was extracted with methylene chloride (100 ml). The combined organic layers were washed with 1N HCl (200 ml), brine (200 ml) then dried and evaporated to a dark oil, 40.6 g. This oil was treated with hot hexane (4×100 ml) and then cyclohexane (100 ml). The combined hexane solutions were allowed to cool to ambient temperature. An off-white solid crystallised, and was isolated by filtration to give 14.2 g of the chloroacetamide, mp 90°–92° C. Recrystallisation from isopropanol gave material of mp 96°–97° C. The above chloroacetamide (10.0 g, 0.34 mol) was suspended in 200 ml of ammonia saturated ethanol, and the mixture heated to 85°–90° C. for 20 hours in a steel bomb. The mixture was cooled to room temperature and the solvent evaporated. The residue was dissolved in 5% NaOH (100 ml) and chloroform (300 ml), the layers separated and the aqueous layer extracted with chloroform (2×50 ml). The combined chloroform extracts were washed with brine (100 ml), dried and evaporated to a dark oil, 13.1 g. This oil was purified by chromatography on a prep. 500 HPLC on silica gel eluting with 5% methanol/chloroform. Pure fractions were combined and evaporated to give 5.9 g of an oil. This was dissolved in ethyl acetate (100 ml) and methanol (25 ml) and treated with maleic acid (2.55 g) and carbon, hot filtered, concentrated to a volume of 60 ml and diluted to 100 ml with ethyl acetate. Upon cooling a white solid crystallised, which was vacuum dried to give 5.76 g of the title compound, mp 150°–151° C.

EXAMPLE 34

Preparation of
2-Amino-N-methyl-N-(1,2-diphenyl-1-methylethyl)acetamide maleate

By procedures essentially the same as those described in Example 33, 2-chloro-N-methyl-N-(1,2-diphenyl-1-methylethyl)acetamide, mp 109°–110° C. and the title compound, mp 166°–168° were prepared.

EXAMPLE 35

Preparation of
2-Amino-N-[1-(3-chlorophenyl)-2-phenyl-1-methylethyl]acetamide maleate To a stirred solution of 2-(3-chlorophenyl)-1-phenyl-2-propylamine (9.0 g, 0.037 mol) in chloroform (100 ml) under nitrogen was added N-(tert-butoxycarbonyl)glycine (7.0 g, 0.04 mol), and then a solution of dicyclohexylcarbodiimide (8.2 g, 0.04 mol) in chloroform (50 ml) and the mixture stirred for 20 hours. The precipitated solid was removed by filtration and the solvent evaporated. The residue was dissolved in ethyl acetate (200 ml) and filtered. The filtrate was washed with 1N HCl (100 ml), 2N sodium carbonate (100 ml) and saturated NaCl (100 ml), dried, then evaporated to an oil, 14.2 g. The above oil was dissolved in ethyl acetate (250 ml), cooled in an ice water bath and the solution was acidified with gaseous HCl. The solution was warmed to ambient temperature and stirred overnight. The solvent was evaporated and the residue was partitioned between chloroform (200 ml) and 3% NaOH (100 ml). The chloroform solution was washed with saturated NaCl (100 ml) and dried over magnesium sulphate. Removal of the solvent gave 10.7 g of an oil. Treatment of this oil with maleic acid (4.1 g, 0.035 mol) in ethyl acetate (300 mnl) gave a white solid which was vacuum dried at 60° C. for 60 hours to give 10.7 g of the title compound, mp 160°–161° C.

EXAMPLE 36

Preparation of
2-Amino-N-[2-(2-chlorophenyl)-1-phenyl-1-methylethyl]acetamide maleate By procedures essentially the same as those described in Example 35 the title compound was prepared. Mp 119°–23° C.

EXAMPLE 37

Preparation of
2-Amino-N-[2-(4-chlorophenyl)-1-phenyl-1-methylethyl]acetamide maleate By procedures essentially the same as those described in Example 35 the title compound was prepared. Mp 162°–164° C.

EXAMPLE 38

Preparation of
2-Amino-N-[1-(2-methylphenyl)-2-phenyl-1-methylethyl]acetamide fumarate By procedures essentially the same as those described in Example 35 the title compound was prepared. Mp 203° C. (D).

EXAMPLE 39

Preparation of
2-Amino-N-[1-(2-chlorophenyl)-2-phenyl-1-methylethyl]acetamide fumarate By procedures essentially the same as those described in Example 35 the title compound was prepared. Mp 209° C. (D).

EXAMPLE 40

Preparation of
2-Amino-N-[2-(3-chlorophenyl)-1-phenyl-1-methylethyl]acetamide maleate By procedures essentially the same as those described in Example 35 the title compound was prepared. Mp 171°–172° C.

EXAMPLE 41

Preparation of
2-Amino-N-[2-(3-aminophenyl)-1-phenyl-1-methylethyl]acetamide fumarate By procedures essentially the same as those described in Example 26 the title compound was prepared. Mp 189°–90° C.

EXAMPLE 42

Preparation of
2-Amino-N-[2-(3-bromophenyl)-1-phenyl-1-methylethyl]acetamide maleate By procedures essentially the same as those described in Example 35 the title compound was prepared. Mp 168°–169° C.

EXAMPLE 43

Preparation of
2-Amino-N-[2-(3-nitrophenyl)-1-phenyl-1-methylethyl]acetamide maleate To a stirred solution of 1-(3-nitrophenyl)-2-phenyl-2-propylamine (10.0 g, 0.039 mol) in dichloromethane (250 ml) under nitrogen was added N-phthaloylglycine (8.87 g, 0.043 mol), and then a solution of dicyclohexylcarbodiimide (8.4 g, 0.041 mol) in dichloromethane (75 ml) and the mixture stirred for 20 hours. The precipitated solid was removed by filtration and the solid evaporated to give 22.3 g of a white solid. This solid was slurried in hot ethanol (200 ml) to provide 16.4 g of 2-(1,3-dioxoisoindol-2-yl)-N-[2-(3-nitrophenyl)-1-phenyl-1-methylethyl]acetamide, mp 172°–173° C. To a stirred suspension of the above compound (8.0 g, 0.018 mol) in absolute ethanol (150 ml) was added 65% hydrazine hydrate (2.0 ml, 0.054 mol) and the mixture was heated to 40° C. for 48 hours. The precipitated solid was removed by filtration and the solvent evaporated. The residue was dissolved in 3% NaOH (200 ml) and extracted with chloroform (3×100 ml). The combined chloroform extracts were dried over magnesium sulphate and the solvent evaporated to an oil 4.3 g. The above oil was dissolved in ethyl acetate (200 ml) and treated with maleic acid (1.7 g, 0.015 mol). The white solid which formed was isolated by filtration and vacuum dried at 50° C. for 128 hours to provide 3.7 g of the title compound, mp 170°–171° C.

EXAMPLE 44

Preparation of
2-Amino-N-[2-phenyl-1-(3-nitrophenyl)-1-methylethyl]acetamide maleate By procedures essentially the same as those described in Example 43, the title compound was prepared. Mp 165°–167° C.

EXAMPLE 45

Preparation of
2-Amino-N-[1-(3-aminophenyl)-2-phenyl-1-methylethyl]acetamide maleate To a stirred solution of 1-phenyl-2-[3-[(2,2,2-trichloroethoxycarbonyl)amino]phenyl]-2-propylamine (9.9 g, 0.025 mol) in chloroform (100 ml) under nitrogen were added N-CBZ-glycine (5.7 g, 0.027 mol) and then a solution of dicyclohexylcarbodiimide (5.6 g, 0.027 mol) in chloroform (70 ml) and the mixture was stirred for 18 hours. The precipitated solid was removed by filtration and the solvent evaporated. The residue was dissolved in ethyl acetate (200 ml) and filtered. The filtrate was washed with 1N HCl (100 ml), 2N sodium carbonate (100 ml), saturated NaCl (100 ml), dried and evaporated to an oil, 15.3 g.

To a solution of the above oil in tetrahydrofuran (150 ml) and 90% acetic acid (150 ml) was added zinc dust (25 g, 0.38 mol) and the mixture stirred at ambient temperature for 20 hours. The reaction mixture was filtered, the filtrate dissolved in water (400 ml) and ethyl acetate (300 ml) and this mixture basified with solid sodium carbonate. The phases were separated and the aqueous phase was extracted with ethyl acetate (200 ml). The combined organic extracts were washed with saturated NaCl (200 ml) and dried over magnesium sulphate. Removal of solvents gave 10.3 g of an oil. This oil was purified by silica gel chromatography on a Waters prep. HPLC, eluting with 50% ethyl acetate/hexane to provide 7.3 g of an oil. This oil was dissolved in methanol (225 ml) and 1N HCl (75 ml), and hydrogenated at 40 psi in a Parr apparatus over 1.8 g of 5% Pd/C catalyst for 2 hours. The catalyst was removed by filtration, and the solvent was evaporated. The residual oil was dissolved in 1N sodium carbonate (150 ml) and extracted with chloroform (3×100 ml). The combined extracts were washed with saturated NaCl (100 ml), dried over magnesium sulphate, and the solvent evaporated to provide an oil, 4.5 g. This oil was dissolved in ethyl acetate (75 ml) and treated with maleic acid (2.1 g, 0.018 mol). The white solid which formed was isolated by filtration and vacuum dried at 60° C. for 48 hours to provide 5.15 g of the title compound, mp 148°–150° C.

EXAMPLE 46

Preparation of
2-Amino-N-[1-(4-chlorophenyl)-2-phenyl-1-methylethyl]acetamide maleate By procedures essentially the same as those described in Example 35, the title compound was prepared. Mp 172.5°–175.5° C.

EXAMPLE 47

Preparation of
2-Amino-N-[1-(3,4-dichlorophenyl)-2-phenyl-1-methylethyl]acetamide maleate By procedures essentially the same as those described in Example 35, the title compound was prepared. Mp 186.5°–87.5° C.

EXAMPLE 48

Preparation of
2-Amino-N-[1-(3,4-dimethoxyphenyl)-2-phenyl-1-methylethyl]acetamide maleate By procedures essentially the same as those described in Example 35, the title compound was prepared. Mp 174.5° C. (D).

EXAMPLE 49

Preparation of
2-Amino-N-[2-(3-cyanophenyl)-1-phenyl-1-methylethyl]acetamide maleate By procedures essentially the same as those described in Example 35, the title compound was prepared. Mp 165°–166° C.

EXAMPLE 50

Preparation of
2-Amino-N-[1-(4-methylphenyl)-2-phenyl-1-methylethyl]acetamide maleate By procedures essentially the same as those described in Example 36, the title compound was prepared. Mp 163° C.

EXAMPLE 51

Preparation of
2-Amino-N-[2-phenyl-1-(4-hydroxyphenyl)-1-methylethyl]acetamide maleate To a stirred solution of 1-phenyl-2-[4-(phenylmethoxy)phenyl]-2-propylamine (3.77 g, 0.012 mol) in dichloromethane (50 ml) under nitrogen were added N-CBZ-glycine (2.47 g, 0.012 mol) and then a solution of dicyclohexylcarbodiimide (2.45 g, 0.012 mol) in dichloromethane (25 ml), and the mixture stirred for 14 hours. The precipitated solid was removed by filtration and the solvent evaporated. The residue was dissolved in ethyl acetate (100 ml) and filtered again. The ethyl acetate solution was washed with 1N HCl, 1N sodium hydroxide, saturated NaCl, dried over magnesium sulphate and the solvent evaporated to give 6.1 g of an oil. This oil was dissolved in ethanol (150 ml), tetrahydrofuran (25 ml) and 1N HCl (50 ml), and hydrogenated at 40 psi in a Parr apparatus over 5% Pd/C (0.9 g) for 4 hours. The catalyst was removed by filtration and the solvents evaporated to give a solid. This solid was suspended in 11N in 1N sodium carbonate (100 ml) and extracted with ethyl acetate (250 ml) containing methanol (50 ml). The organic solution was washed with saturated sodium chloride solution, dried over magnesium sulphate and the solvent evaporated to leave a white solid, 1.82 g. This solid was dissolved in methanol (100 ml) and maleic acid (0.74 g, 0.0064 mol) was added. The solvent was evaporated to an oil. This oil was crystallised from ethyl acetate-methanol and vacuum dried to provide 1.91 g of the title compound, mp 174°–175° C.

EXAMPLE 52

Preparation of 2-Amino-N-[1-(4-hydroxyphenyl)-2-phenylethyl]acetamide maleate

By procedures essentially the same as those described in Example 51 the title compound was prepared. Mp 184°–185° C.

EXAMPLE 53

Preparation of
2-Amino-N-[2-(4-hydroxyphenyl)-1-phenyl-1-methylethyl]acetamide maleate By procedures essentially the same as those described in Example 51 the title compound was prepared. Mp 167°–168° C.

EXAMPLE 54

Preparation of 2-Amino-N-[2-(4-hydroxyphenyl)-1-phenylethyl]acetamide acetate

To a stirred solution of 2-[4-(phenylmethoxy)phenyl]-1-phenylethylamine (6.51 g, 0.022 mol) in chloroform (100 ml) under nitrogen were added N-CBZ-glycine (4.35 g, 0.021 mol) and then a solution of dicyclohexylcarbodiimide (4.42 g, 0.021 mol) in chloroform (50 ml) and the mixture stirred for 24 hours. The precipitated solid was removed by filtration. The filter cake was suspended in warm tetrahydrofuran (150 ml) and the insoluble material was removed by filtration. The filtrates were combined and the solvents evaporated to a white solid, 10.7 g. This solid was recrystallised from ethyl acetate and cyclohexane to provide 8.5 g of a white solid, mp 155°–157° C. This solid was dissolved in tetrahydrofuran (300 ml) and acetic acid (70 ml) and hydrogenated at 40 psi in a Parr apparatus over 5% Pd/C (1.5 g) for 17 hours. The catalyst was removed by filtration and the solvent evaporated to leave a white solid. This solid was recrystallised twice from ethyl acetate and methanol, and vacuum dried to provide 2.53 g of the title compound, mp 145°–147° C.

EXAMPLE 55

Preparation of
2-Amino-N-[1,2-bis(4-hydroxyphenyl)-1-methylethyl]acetamide acetate By procedures essentially the same as those described in Example 54 the title compound was prepared. Mp 225°–228° C. (D).

EXAMPLE 56

Preparation of
2-Amino-N-[1,2-bis(4-hydroxyphenyl)ethyl]acetamide acetate

By procedures essentially the same as those described in Example 54 the title compound was prepared. Mp 192°–193° C.

EXAMPLE 57

Preparation of
2-Amino-N-[1-(3-methoxyphenyl)-2-phenyl-1-methylethyl]acetamide maleate By procedures essentially the same as those described in Example 54 the title compound was prepared. Mp 150° C.

EXAMPLE 58

Preparation of
2-Amino-N-[1-(4-methoxyphenyl)-2-phenyl-1-methylethyl]acetamide maleate By procedures essentially the same as those described in Example 43 the title compound was prepared. Mp 157°–158° C.

EXAMPLE 59

Preparation of
2-Amino-N-[2-(3,4-dichlorophenyl)-1-phenyl-1-methylethyl]acetamide maleate By procedures essentially the same as those described in Example 35 the title compound was prepared. Mp 172.5°–174° C.

EXAMPLE 60

Preparation of
2-Amino-N-[2-(4-methoxyphenyl)-1-phenyl-1-methylethyl]acetamide maleate By procedures essentially the same as those described in Example 43 the title compound was prepared. Mp 165°–167° C.

What we claim is:
1. A compound of formula IA:

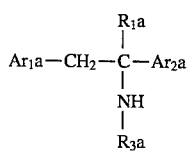

wherein
Ar$_1$a and Ar$_2$a, which may be the same or different, independently represent phenyl or phenyl substituted by one or more of nitro, halogen, hydroxy, C1 to 6 alkoxy, C1 to 6 alkyl or cyano; or 2-, 3-, or 4-pyridinyl;
R$_1$a represents C1 to 6 alkyl or C1 to 6 alkoxycarbonyl;
R$_3$a represents hydrogen or C1 to 6 alkyl;
provided Ar$_1$a and Ar$_2$a do not both represent unsubstituted phenyl;
or a pharmaceutically acceptable salt thereof.

2. A compound according to claim 1 where either one or both of Ar$_1$a and Ar$_2$a represents 4-hydroxyphenyl.

3. A compound according to claim 1 in which Ar$_1$a and Ar$_2$a are mono- or disubstituted.

4. A compound according to claim 1 wherein R$_1$a represents methyl.

5. A compound according to claim 1 where R$_3$a represents hydrogen.

6. A pharmaceutical composition comprising a compound of formula IA as defined in claim 1, or a pharmaceutically acceptable salt thereof, in admixture with a pharmaceutically acceptable adjuvant, diluent or carrier.

7. A compound according to claim 1 wherein the compound is 1-(4-hydroxyphenyl)-2-phenyl-2-propylamine, or a pharmaceutically acceptable salt thereof.

8. A compound according to claim 1 wherein the compound is 1-phenyl-2-(4-hydroxyphenyl)-2-propylamine, or a pharmaceutically acceptable salt thereof.

9. A compound according to claim 1 wherein the compound is 1,2-bis(4-hydroxyphenyl)-2-propylamine, or a pharmaceutically acceptable salt thereof.

10. A compound according to claim 1 wherein the compound is 1-(3-nitrophenyl)-2-phenyl-2-propylamine, or a pharmaceutically acceptable salt thereof.

11. A compound according to claim 1 wherein the compound is 1-(3-chlorophenyl)-2-phenyl-2-propylamine, or a pharmaceutically acceptable salt thereof.

12. A compound according to claim 1 wherein the compound is 1-(3-bromophenyl)-2-phenyl-2-propylamine, or a pharmaceutically acceptable salt thereof.

13. A compound according to claim 1 wherein the compound is 1-(3-cyanophenyl)-2-phenyl-2-propylamine, or a pharmaceutically acceptable salt thereof.

14. A compound according to claim 1 wherein the compound is 2-(2-methylphenyl)-1-phenyl-1-propylamine, or a pharmaceutically acceptable salt thereof.

15. A compound according to claim 1 wherein the compound is 1-(4-chlorophenyl)-2-phenyl-2-propylamine, or a pharmaceutically acceptable salt thereof.

16. A compound according to claim 1 wherein the compound is 1-phenyl-2-(3,4-dichlorophenyl)-2-propylamine, or a pharmaceutically acceptable salt thereof.

17. A compound according to claim 1 wherein the compound is 2-(3-chlorophenyl)-1-phenyl-2-propylamine, or a pharmaceutically acceptable salt thereof.

18. A compound according to claim 1 wherein the compound is 1-(2-chlorophenyl)-2-phenyl-2-propylamine, or a pharmaceutically acceptable salt thereof.

19. A compound according to claim 1 wherein the compound is 2-(2-chlorophenyl)-1-phenyl-2-propylamine, or a pharmaceutically acceptable salt thereof.

20. A compound according to claim 1 wherein the compound is 2-(3-nitrophenyl)-1-phenyl-2-propylamine, or a pharmaceutically acceptable salt thereof.

21. A compound according to claim 1 wherein the compound is 2-(4-chlorophenyl)-1-phenyl-2-propylamine, or a pharmaceutically acceptable salt thereof.

22. A compound according to claim 1 wherein the compound is 2-(3,4-dimethoxyphenyl)-1-phenyl-2-propylamine, or a pharmaceutically acceptable salt thereof.

23. A compound according to claim 1 wherein the compound is 2-(4-methylphenyl)-1-phenyl-2-propylamine, or a pharmaceutically acceptable salt thereof.

24. A compound according to claim 1 wherein the compound is 2-(4-methoxyphenyl)-1-phenyl-2-propylamine, or a pharmaceutically acceptable salt thereof.

25. A compound according to claim 1 wherein the compound is 1-(3,4-dichlorophenyl)-2-phenyl-2-propylamine, or a pharmaceutically acceptable salt thereof.

26. A compound according to claim 1 wherein the compound is 1-(4-methoxyphenyl)-2-phenyl-2-propylamine, or a pharmaceutically acceptable salt thereof.

27. A compound according to claim 1 wherein the compound is 1-phenyl-2-(3-methoxyphenyl)-2-propylamine, or a pharmaceutically acceptable salt thereof.

* * * * *